(12) United States Patent
Grady et al.

(10) Patent No.: US 11,742,070 B2
(45) Date of Patent: Aug. 29, 2023

(54) SYSTEM AND METHOD FOR CONTROLLING USER REPEATABILITY AND REPRODUCIBILITY OF AUTOMATED IMAGE ANNOTATION CORRECTION

(71) Applicant: HeartFlow, Inc., Redwood City, CA (US)

(72) Inventors: Leo Grady, Millbrae, CA (US); Michiel Schaap, Redwood City, CA (US)

(73) Assignee: HeartFlow, Inc., Mountain View, CA (US)

( * ) Notice: Subject to any disclaimer, the term of this patent is extended or adjusted under 35 U.S.C. 154(b) by 63 days.

(21) Appl. No.: 16/725,649

(22) Filed: Dec. 23, 2019

(65) Prior Publication Data

US 2020/0134897 A1    Apr. 30, 2020

Related U.S. Application Data

(63) Continuation of application No. 15/834,488, filed on Dec. 7, 2017, now Pat. No. 10,546,403, which is a
(Continued)

(51) Int. Cl.
*G16H 30/40* (2018.01)
*G06F 16/58* (2019.01)
(Continued)

(52) U.S. Cl.
CPC ......... *G16H 30/40* (2018.01); *G06F 3/04842* (2013.01); *G06F 3/04845* (2013.01);
(Continued)

(58) Field of Classification Search
None
See application file for complete search history.

(56) References Cited

U.S. PATENT DOCUMENTS

| 6,504,951 | B1 | 1/2003 | Luo et al. |
| 6,512,846 | B1 | 1/2003 | Luo |
| 7,809,190 | B2 | 10/2010 | Rousson et al. |
| 8,364,673 | B2 | 1/2013 | Chang et al. |
| 8,463,045 | B2 | 6/2013 | Yang et al. |

(Continued)

FOREIGN PATENT DOCUMENTS

| EP | 2008578 A1 | 12/2008 |
| WO | 2006128302 A1 | 12/2006 |
| WO | 2013040693 A1 | 3/2013 |

OTHER PUBLICATIONS

Yang et al, Automatic centerline extraction of coronary arteries in coronary computed tomographic angiography, Int J Cardiovasc Imaging (2012) 28:921-933 (Year: 2012).*

(Continued)

*Primary Examiner* — Andrae S Allison
(74) *Attorney, Agent, or Firm* — Bookoff McAndrews, PLLC

(57) ABSTRACT

Systems and methods are disclosed for controlling image annotation. One method includes acquiring a digital representation of image data and generating a set of image annotations for the digital representation of the image data. The method also may include determining an association between members of the set of image annotations and generating one or more groups of members based on the association. A representative annotation from the one or more groups may also be determined, presented for selection, and the selection may be recorded in memory.

20 Claims, 7 Drawing Sheets

Related U.S. Application Data continuation of application No. 15/415,264, filed on Jan. 25, 2017, now Pat. No. 9,870,634, which is a continuation of application No. 14/470,314, filed on Aug. 27, 2014, now Pat. No. 9,589,349.

(60) Provisional application No. 61/882,512, filed on Sep. 25, 2013.

(51) Int. Cl.
    *G06T 7/00*           (2017.01)
    *G06F 3/04842*     (2022.01)
    *G06F 3/04845*     (2022.01)
    *G06T 11/60*        (2006.01)
    *G16H 30/20*       (2018.01)

(52) U.S. Cl.
    CPC ........ *G06F 16/5866* (2019.01); *G06T 7/0012* (2013.01); *G06T 7/97* (2017.01); *G06T 11/60* (2013.01); *G16H 30/20* (2018.01); *G06T 2207/10004* (2013.01); *G06T 2207/30004* (2013.01)

(56) References Cited

U.S. PATENT DOCUMENTS

| | | | |
|---|---|---|---|
| 8,532,377 B2 | 9/2013 | Skaff et al. | |
| 9,589,349 B2 | 3/2017 | Grady et al. | |
| 2005/0201619 A1 | 9/2005 | Sun et al. | |
| 2006/0171586 A1 | 8/2006 | Georgescu et al. | |
| 2006/0239554 A1* | 10/2006 | Sun | G06T 19/00 382/173 |
| 2006/0274928 A1 | 12/2006 | Collins | |
| 2007/0052724 A1* | 3/2007 | Graham | G06T 19/003 345/620 |
| 2007/0253611 A1* | 11/2007 | Rousson | G06K 9/34 382/128 |
| 2008/0044072 A1* | 2/2008 | Kiraly | G06T 7/11 382/128 |
| 2008/0091670 A1* | 4/2008 | Ismalon | G06F 16/3322 |
| 2008/0195657 A1 | 8/2008 | Naaman et al. | |
| 2009/0177460 A1 | 7/2009 | Huang et al. | |
| 2009/0278846 A1 | 11/2009 | Gulsun | |
| 2010/0260396 A1 | 10/2010 | Brandt et al. | |
| 2011/0026793 A1* | 2/2011 | Goel | G06T 7/60 382/131 |
| 2011/0182493 A1 | 7/2011 | Huber et al. | |
| 2012/0027273 A1 | 2/2012 | Zankowski | |
| 2012/0172700 A1 | 7/2012 | Krishnan et al. | |
| 2012/0176412 A1 | 7/2012 | Stuebe et al. | |
| 2012/0269436 A1 | 10/2012 | Mensink et al. | |
| 2013/0110838 A1 | 5/2013 | Lidy et al. | |
| 2013/0315458 A1 | 11/2013 | Beymer | |
| 2014/0143643 A1* | 5/2014 | Ayed | G16H 30/40 715/202 |
| 2014/0226889 A1 | 8/2014 | Liu et al. | |
| 2016/0104281 A1* | 4/2016 | Grady | G06T 17/00 382/128 |
| 2018/0060533 A1* | 3/2018 | Reicher | G16H 15/00 |
| 2018/0068221 A1* | 3/2018 | Brennan | G06N 20/00 |
| 2018/0068222 A1* | 3/2018 | Brennan | G06N 5/022 |

OTHER PUBLICATIONS

Schneider et al, Joint 3-D vessel segmentation and centerline extraction using oblique Hough forests with steerable filters,. Medical Image Analysis 19 (2015) 220-249 (Year: 2015).*

Hadjiiski, Lubomir, et al. "Automated registration of coronary arterial trees from multiple phases in coronary CT angiography (cCTA)." Medical Imaging 2013: Computer-Aided Diagnosis. vol. 8670. SPIE, Mar. 2013. (Year: 2013).*

Wolterink, Jelmer M., et al. "Coronary artery centerline extraction in cardiac CT angiography using a CNN-based orientation classifier." Medical image analysis 51 (2019): 46-60. (Year: 2019).*

Bauer et al, "Edge Based Tube Detection for Coronary Artery Centerline Extraction", , Jul. 22, 2008.

Charles A. Taylor et al., Computational Fluid Dynamics Applied to Cardiac Computed Tomography for Noninvasive Quantification of Fractional Flow Reserve, Journal of the American College of Cardiology, vol. 61, No. 22, pp. 2233-2241 (Jun. 4, 2013).

Cristian Lorenz et al., A comprehensive shape model of the heart, Medical Image Analysis 10, pp. 657-670, (2006).

Hernandez-Vela, A.; Gatta, C.; Escalera, S.; Igual, L.; Martin-Yuste, V.; Sabate, M.; Radeva, P., "Accurate Coronary Centerline Extraction, Caliber Estimation, and Catheter Detection in Angiographies," in Information Technology in Biomedicine, IEEE Transactions on , vol. 16, No. 6, pp. 1332-1340, Nov. 2012.

Hortense A. Kirisli et al., Fully automatic cardiac segmentation from 3D CTA data: a multi-atlas based approach, Proc. of SPIE, vol. 7623.

Michiel Schaap et al., Robust Shape Regression for Supervised Vessel Segmentation and its Application to Coronary Segmentation in CTA, IEEE Transactions on Medical Imaging, vol. 30, No. 11, pp. 1974-1986, (Nov. 2011).

Search Report and Written Opinion issued in International Application No. PCT/US2014/053065, filed Aug. 28, 2014, dated Feb. 5, 2015 (16 pages).

Tang et al, Semiautomatic carotid lumen segmentation for quantification of lumen geometry in multispectral MRI, Medical Image Analysis vol. 16, Issue 6, Aug. 2012, pp. 1202-1215.

Wang et al, Integrating automatic and interactive methods for coronary artery segmentation: let the PACS workstation think ahead, Int J CARS (2010) 5:275-285.

Yang et al "Automatic centerline extraction of coronary arteries in coronary computed tomographic angiography" Int J Cardiovasc Imaging (2012) 28:921-933.

Yefeng Zheng et al., Efficient Detection of Native and Bypass Coronary Ostia in Cardiac CT Volumes: Anatomoical vs. Pathological Structures.

Yefeng Zheng et al., Four-Chamber Heart Modeling and Automatic Segmentation for 3-D Cardiac CT Volumes Using Marginal Space Learning and Steerable Features, IEEE Transactions on Medical Imaging, vol. 27, No. 11, pp. 1668-1681 (Nov. 2008).

Yoshiro Kitamura et al., Automatic Coronary Extraction by Supervised Detection and Shape Matching, IEEE, pp. 234-237 (2012).

Wenyin, L., Dumais, S. T., Sun, Y., Zhang, H., Czerwinski, M., & Field, B. A. (Jul. 2001). Semi-Automatic Image Annotation. In Interact (vol. 1, pp. 326-333). (Year: 2001).

Moehrmann, Julia, and Gunther Heldemann. "Interactive Image Annotation with Visual Feedback.", 2014, <http://vision.cs.utexas.edu/hmcv2014/moehrmann_heidemann_hmcv20 14.pdf> (Year: 2014).

Sun, Shanhui. "Automated and interactive approaches for optimal surface finding based segmentation of medical image data." PhD (Doctor of Philosophy) thesis, University of Iowa, 2012. https://doi.org/10.17077/etd.o2bmvzlw.

L. Wang et al., "A General Framework for Context-Specific Image Segmentation Using Reinforcement Learning," in *IEEE Transactions on Medical Imaging*, vol. 32, No. 5, pp. 943-956, May 2013, doi: 10.1109/TMI.2013.2252431 (14 pages).

Iker Gondra et al., "A multiple instance learning based framework for semantic image segmentation," Multimed Tools Appl (2010) 48:339-365,DOI 10.1007/s11042-009-0347-z (27 pages).

\* cited by examiner

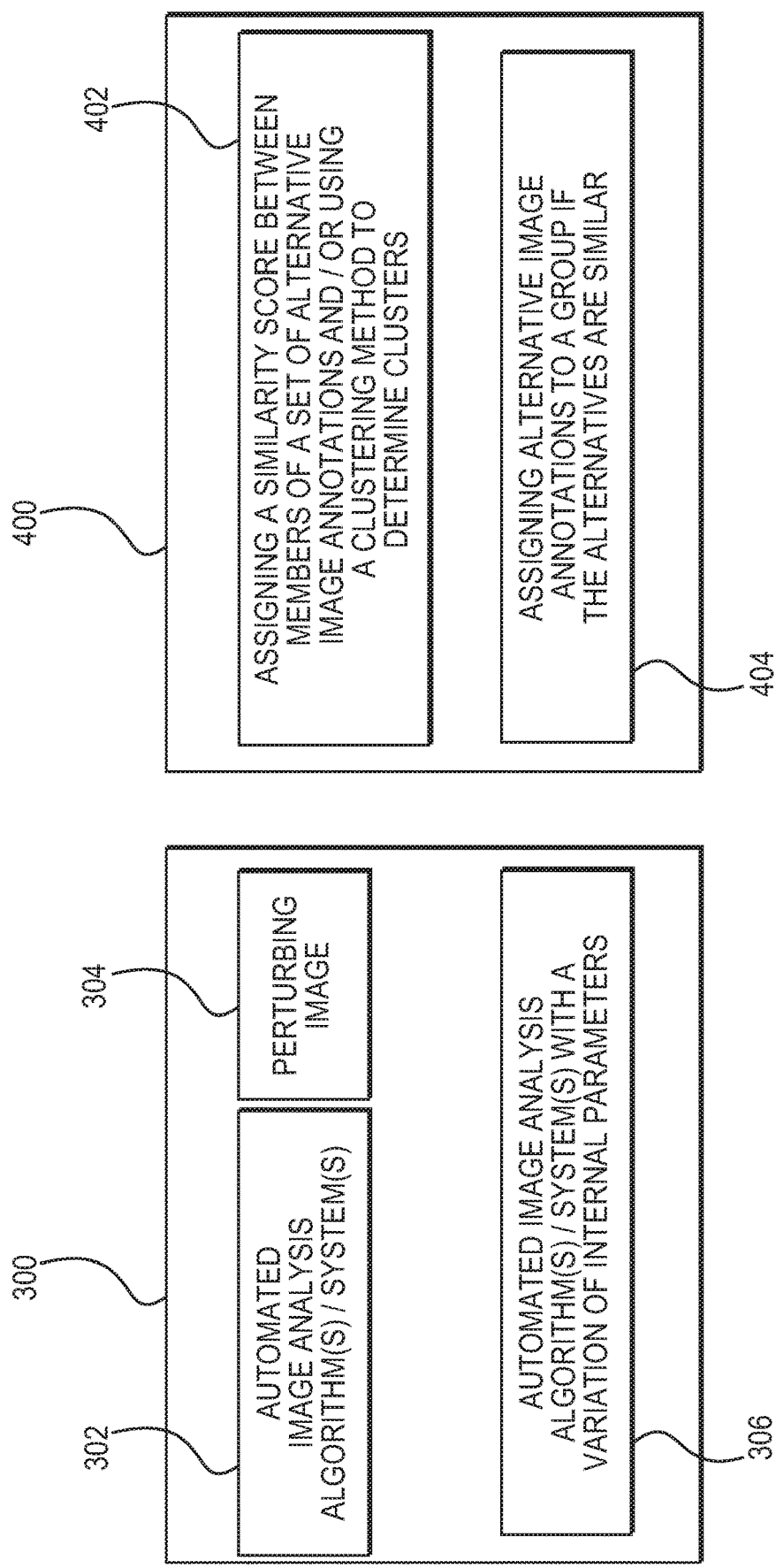

SYSTEM AND METHOD FOR CONTROLLING USER REPEATABILITY AND REPRODUCIBILITY OF AUTOMATED IMAGE ANNOTATION CORRECTION

RELATED APPLICATION

This application is a continuation of and claims the benefit of priority to U.S. application Ser. No. 15/834,488 filed on Dec. 7, 2017, which is a continuation of and claims the benefit of priority to U.S. patent application Ser. No. 15/415,264, filed Jan. 25, 2017 (now U.S. Pat. No. 9,870,634, issued Jan. 16, 2018), which is a continuation of and claims the benefit of priority to U.S. patent application Ser. No. 14/470,314, filed on Aug. 27, 2014 (now U.S. Pat. No. 9,589,349, issued Mar. 7, 2017), which claims the benefit of priority from U.S. Provisional Application No. 61/882,512, filed Sep. 25, 2013, each of which is hereby incorporated herein by reference in its entirety.

FIELD

Various embodiments of the present disclosure relate generally to medical imaging and related methods. More specifically, particular embodiments of the present disclosure relate to systems and methods for controlling user repeatability and reproducibility of automated image annotation correction.

BACKGROUND

Automated image annotation plays an increasing role in commercial systems. In particular, the medical imaging community relies increasingly on the automated analysis and annotation of large images. Since this automated image analysis may be used to drive patient care decisions, it can be important for the automated results to be validated and appropriately corrected (if necessary) by a knowledgeable user. The user may be a medical doctor, technician, or another individual trained to evaluate medical images and use the software. Outside of a medical context, the user may be anyone who evaluates the image annotations, including either professionals or consumers.

In a commercial context, a particular concern is the ability of a user to provide corrections of automated image annotations, which are repeatable and reproducible from one user to another or from a user to themselves. Particularly in a medical context, diagnosis and treatment decisions may be made on the basis of the (corrected) medical image annotations, so it is important to minimize any dependence of the image annotation corrections on the user. Manual tools for correcting automated image annotations (e.g., picking points, drawing lines, drawing shapes (e.g. polygons or circles), modifying pixel labels, using free text to adjust annotation labels) are subject to substantial levels of inter-user and intra-user variability, which should be controlled in order to provide a reliable image annotation system that maximizes patient benefit.

Thus, a need exists for systems and methods to decrease variability and control user repeatability and reproducibility of automated image annotations.

The foregoing general description and the following detailed description are exemplary and explanatory only and are not restrictive of the disclosure.

SUMMARY

According to certain aspects of the present disclosure, systems and methods are disclosed for controlling image annotations using a computer system. One method includes using a processor for acquiring a digital representation of image data; generating a set of image annotations for the digital representation of the image data; determining an association between members of the set of image annotations and generating one or more groups of members based on the associations; determining a representative annotation from each of the one or more groups; presenting the one or more representative annotations for selection; and recording the selection and saving the one or more representative annotations in memory.

According to certain additional aspects of the present disclosure, one method for controlling image annotations using a computer system, may include one or more of: further comprising the following steps prior to the step of generating a set of image annotations for the digital representation of the image data: presenting an automated annotation of the digital representation for validation and/or correction, and receiving a user input of an image annotation based on the user's evaluation of the automated annotation; wherein the image data is of a target object; wherein the target object is a portion of a body organ; wherein the digital representation of the image data is acquired electronically via a network; wherein the set of alternative image annotations are electronically automatically generated; wherein the set of alternative image annotations are generated using multiple image analysis algorithms; wherein the association between members of the set of alternative image annotations is determined by assigning a similarity score between the members; wherein the association between members of the set of alternative image annotations is determined by assigning alternative image annotations to a group if the alternatives are the same; wherein the automated image annotation comprises a polygon (e.g. a box) around a target feature; and further comprising applying a k-means algorithm to a centroid of the box.

In accordance with another aspect, disclosed is a system of controlling image annotations, the system comprises: a data storage device storing instructions for controlling image annotation; and a processor configured to execute the instructions to perform a method including: acquiring a digital representation of image data; generating a set of image annotations for the digital representation of the image data; determining an association between members of the set of image annotations and generating one or more groups of members based on the associations; determining a representative annotation from each of the one or more groups; presenting the one or more representative annotations for selection; and recording the selection and saving the one or more representative annotations in memory.

According to certain additional examples of the present disclosure, one system of controlling image annotation, may include one or more of the following aspects: further comprising the following steps prior to the step of generating a set of image annotations for the digital representation of the image data: presenting an automated annotation of the digital representation for validation and/or correction, and receiving a user input of an image annotation based on the user's evaluation of the automated annotation; wherein the image data is of a target object; wherein the processor is further configured to electronically acquire the digital representation of image data via a network; wherein the processor is further configured to automatically generate the set of alternative image annotations; wherein the processor is further configured to automatically generate the set of alternative image annotation using multiple image analysis algorithms; wherein the processor in configured to determine the association between members of the set of alternative image annotations by assigning a similarity score between the members; wherein processor is configured to determine the association between members of the set of alternative image annotations by assigning alternative image annotations to a group if the alternatives are the same; and wherein the processor is configured to generate a box around a target feature.

In accordance with yet another embodiment, a non-transitory computer readable medium for use on a computer system containing computer-executable programming instructions for controlling image annotations, the instructions being executable by the computer system for: acquiring a digital representation of image data; generating a set of image annotations for the digital representation of the image data; determining an association between members of the set of image annotations and generating one or more groups of members based on the associations; determining a representative annotation from each of the one or more groups; presenting the one or more representative annotations for selection; and recording the selection and saving the one or more representative annotations in memory.

According to certain additional examples of the present disclosure, one non-transitory computer-readable medium for use on a computer system containing computer-executable programming instructions for controlling image annotations, the instructions being executable by the computer system for determining an association between members of the set of alternative image annotations and generating one or more groups of members based on the associations, wherein the association between members of the set of alternative image annotations is determined by assigning a similarity score between the members.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 3 is a block diagram of exemplary options for generating a set of alternative image annotations, according to an exemplary embodiment of the present disclosure.

FIG. 4 is a block diagram of exemplary options for determining an association between members of a set of alternative image annotations.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

As described above, correction of digital images may be desired to provide a clearer or more accurate depiction of a target object.

The present disclosure is directed to systems and methods for controlling user repeatability and reproducibility for automated image annotation correction. The systems and methods involve presenting the user with various alternative annotations of a digital image of a target object. The user may select one or more of the alternative annotations to validate an automated annotation and/or correct an erroneous image annotation. Therefore, instead of directly correcting an automated image annotation, the user may be presented with alternative solutions that may be selected to correct the automated image annotation. This process of correcting an image annotation by selection from alternatives rather than the user directly correcting the annotation may dramatically improve the reproducibility and repeatability of the correction process by reducing variability in user annotations and may increase efficiencies in obtaining a correct image annotation. In addition, the user selections may be processed and used by suitable data analysis tools to improve the automated image annotations so as to produce more accurate results.

Figure 1:
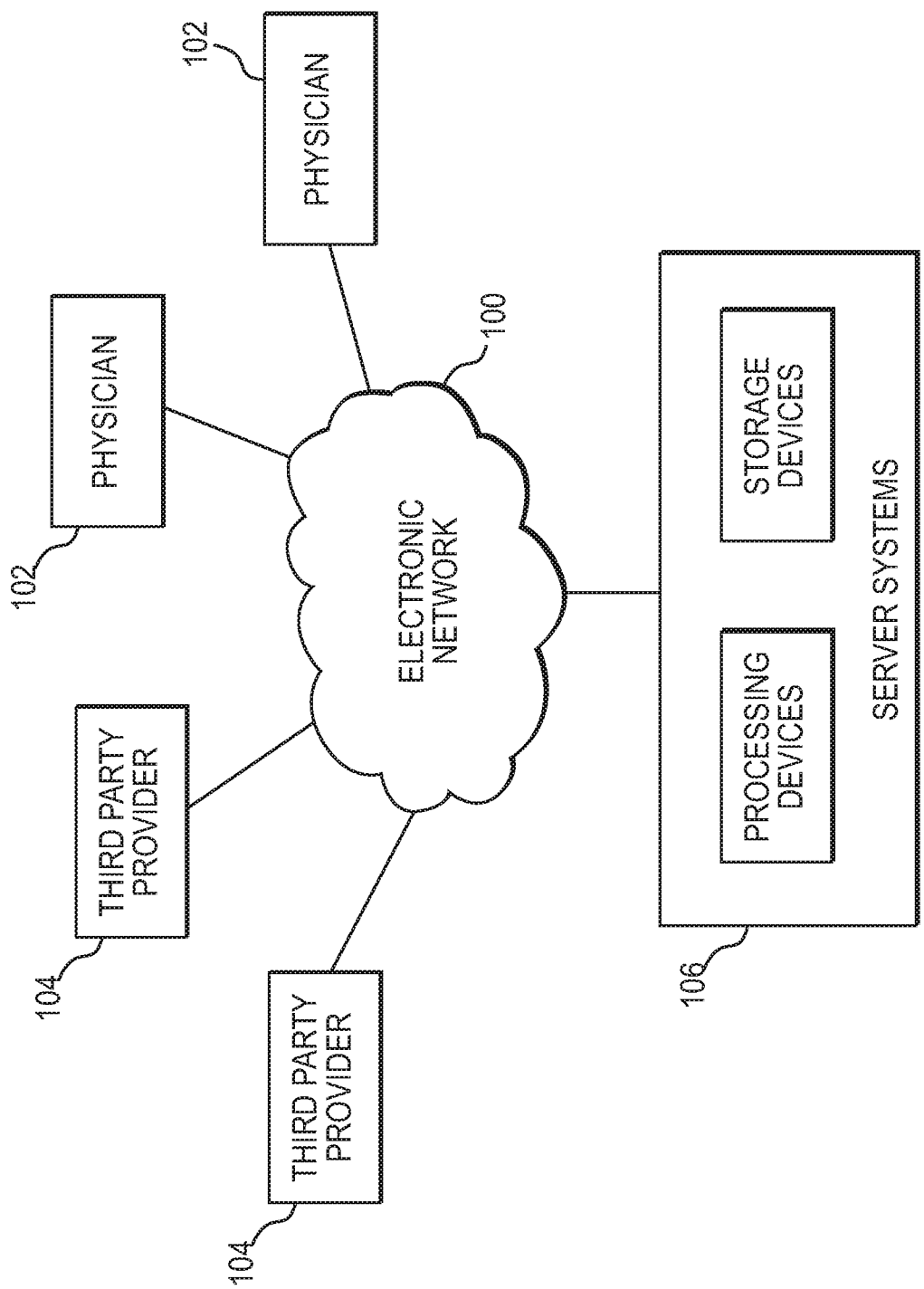
FIG. 1 is a block diagram of an exemplary system and network for controlling user repeatability and reproducibility of automated image annotation correction.

Referring now to the figures, FIG. 1 depicts a block diagram of an exemplary system and network for controlling user repeatability and reproducibility of automated image annotation correction. Specifically, FIG. 1 depicts a plurality of physicians of other healthcare professionals 102 and third party providers 104, any of whom may be connected to an internal or external electronic network 100, such as the Internet, through one or more computers, servers, and/or handheld mobile devices. Physicians 102 and/or third party providers 104 may create or otherwise obtain images of one or more target regions of one or more patients. For example, images of one or more patients' cardiac systems, vascular systems, neurological systems, etc., may be created or obtained by any suitable imaging devices. The physicians 102 and/or third party providers 104 may also obtain any combination of patient-specific information, such as age, medical history, blood pressure, blood viscosity, etc. This information may be directly obtained by examination of the patient or retrieved from the patient's medical record, such by electronically accessing the patient's electronic medical record. In some examples, the third party provider 104 may be an imaging laboratory and the patient-specific information (e.g. medical history, current treatment plan, family history) may be electronically retrieved (e.g. automatically) via the electronic network 100, e.g. via the Internet. Physicians 102 and/or third party providers 104 may transmit the images, such as cardiac and/or vascular images, and/or patient-specific information to server systems 106 over the electronic network 100. The electronic network 100 may include various security components for validating and securing the privacy of the patient-specific information transmitted and complying with all pertinent laws and regulations. For example, the electronic network 100 may encrypt or encode the patient's identity by removing any identifying information (e.g. patient name, address, social security number, phone number, etc.) and replacing this information with an identification code that is generated, transmitted, and saved in digital memory. In this and any other suitable manner that complies with applicable health information patient privacy rules, the privacy of the patient may be maintained. In addition, the digital image representations also may be encrypted or encoded.

This electronic transmission of data may occur at any suitable time. For example, the images may be electronically locally saved on one or more digital storage devices at the physician 102 or third party provider 104 and the data, which may be electronically encrypted, may be transmitted at a later time, or the data may be transmitted as soon as the information is obtained. In some embodiments, portions of the data may be transmitted at different times. For example, the patient-specific information may be transmitted before or after the image is transmitted. The data may be encoded in any suitable manner and may be decoded or parsed using one or more processors having program instructions configured to electronically/digitally decode/decrypt and/or parse the data. Server systems 106 may include storage devices for storing images and data received from physicians 102 and/or third party providers 104. Server systems 106 also may include processing devices (e.g. one or a network of multiple processors) for processing images and data stored in the storage devices.

Figure 2:
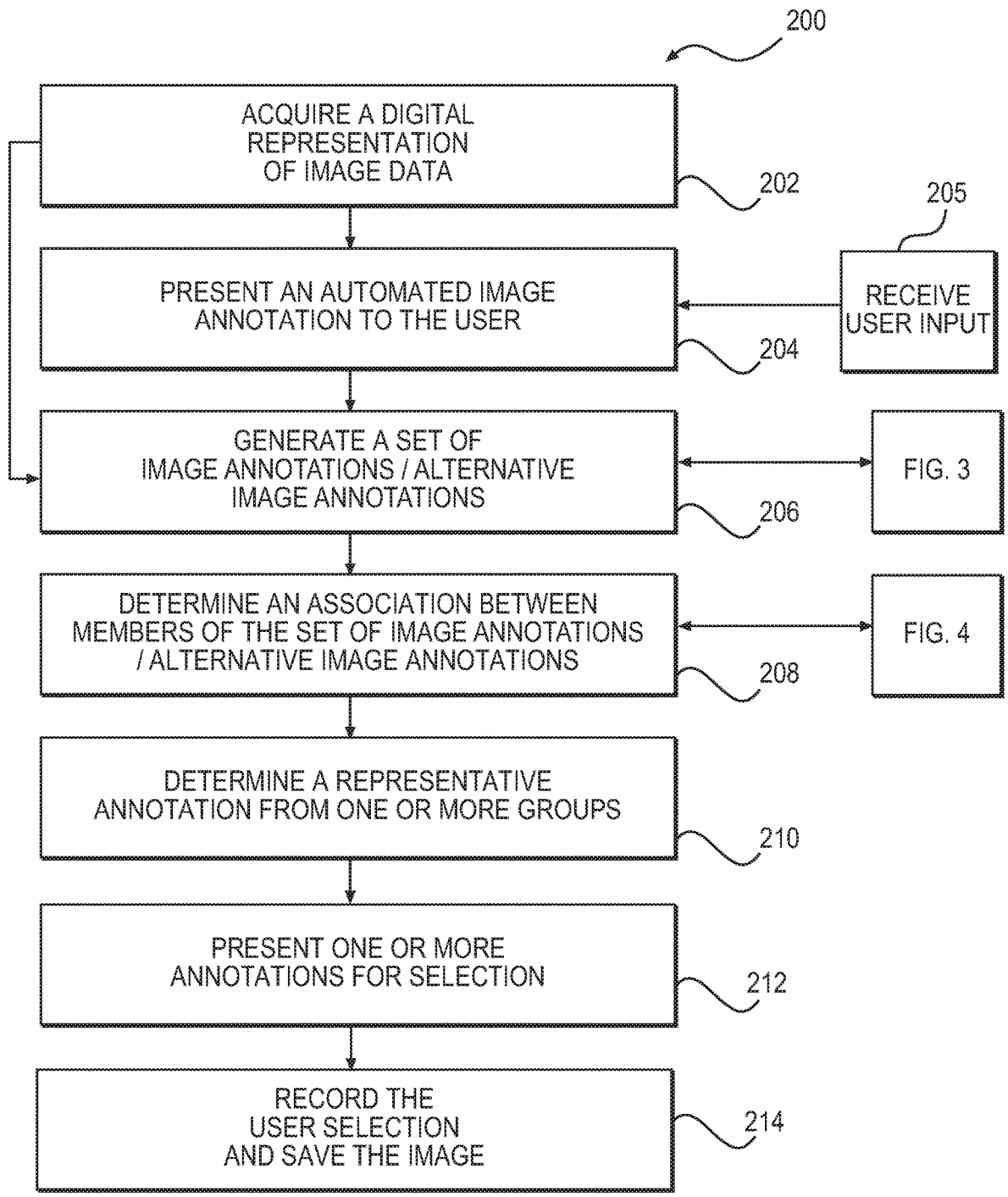
FIG. 2 is a block diagram of an exemplary method for presenting alternative image annotations to a user, according to an exemplary embodiment of the present disclosure.

FIG. 2 is a block diagram of an exemplary method 200 for controlling user repeatability and reproducibility for automated image annotation correction. Method 200 may be performed by the server systems 106, based on information, images, and data received from physicians 102 and/or third party providers 104 over the electronic network 100. The method 200 may include various steps 202-214 which may result in the user providing electronic feedback, such as validation and/or correction of an automated image annotation by making selections from a group of alternative image annotations. This may improve the repeatability and reproducibility of automated image annotation correction.

The method 200 may include acquiring a digital representation of image data at step 202. The image may be of any suitable target, such as an organ or portion of a patient's body, or any other suitable target. For example, the target may be a portion of the heart, lungs, brain, etc. The image of the target may be obtained using any suitable technology, such as an electronic scan from computed tomography, magnetic resonance images, ultrasound images, images from a 3-D scanner, etc.

In one embodiment, the method 200 may be used for modeling and simulation for blood flow of the heart (Taylor, Fonte, & Min, "Computational Fluid Dynamics Applied to Cardiac Computed Tomography for Noninvasive Quantification of Fractional Flow Reserve" J Am Coll Cardiol. 2013; 61(22):2233-2241 the disclosure of which is incorporated herein by reference in its entirety), which may involve an extremely precise image segmentation from a cardiac CT image to create a patient-specific 3-D geometric model of the patient's heart. This 3-D model may be validated and corrected by trained users either local or remote to server systems 106, by using the methods disclosed herein in order to control the repeatability and reproducibility of automated image annotation correction and ensure the accuracy of the blood flow simulations and the treatment decisions derived from the simulation.

The digital representation of the image may be acquired at step 202. The digital representation of the image may have been previously transmitted by the physician 102 or the third party provider 104 to an electronic storage device. The digital representation electronically transmitted by the physician 102 of the third party provider 104 may be automatically electronically encrypted. The digital representation of the image may then be retrieved from the digital storage, such as a hard drive, network drive, remote server, etc. of any suitable computational device, such as by a connected computer, laptop, digital signal processor (DSP), server etc., and may be automatically electronically decrypted. The digital representation of the image may be retrieved from the memory or digital storage in any suitable manner. For example, a computational device may include programming with instructions to request the digital representation from the memory or the digital storage at a certain time and send it to the computational device of the user, such as a technician, at a certain time.

The digital representation of the image data acquired at step 202 may then be processed by one or more computational devices. In some embodiments, a set of image annotations maybe directly generated for the digital representation of the image data at step 206. Alternatively, following the acquisition of the digital representation of image data at step 202, an automated annotation of the digital representation may be presented to the user for validation and or correction at step 204 and the user's input at step 205 may be automatically electronically processed. The term image annotation can generically represent any identification in an image (including, but not limited to, a 2-D image, a 3-D image, or an image of greater dimension) that includes a localization or a labeling. Examples may include: localization of particular points (landmarks), localization of lines (e.g., diameters, centerlines), 2-D regions of interest (a 2-D segmentation), 3-D regions of interest (a 3-D segmentation), an n-D region of interest (an n-D segmentation), an n-D+ time region of interest (an n-D segmentation tracked through time) or a labeling of one or more identified structures.

The automated image annotation at step 204 may be generated by applying an automated image analysis system. The automated image analysis system may be any suitable automated image analysis system and may include various annotations. In one example, the automated image analysis system may annotate a 3-D segmentation of the aorta (e.g., using (Kirisli, et al., "Fully automatic cardiac segmentation from 3D CTA data: a multi-atlas based approach," Proc. of SPIE Vol. 7623 762305-9, 2010), the disclosure of which is incorporated herein by reference in its entirety). In another example, the automated image analysis system may annotate the location of ostial points (e.g., using (Zheng, Tek, Funka-Lea, Zhou, Vega-Higuera, & Comaniciu, "Efficient Detection of Native and Bypass Coronary Ostia in Cardiac CT Volumes: Anatomical vs. Pathological Structures," Proc. Intl Conf. Medical Image Computing and Computer Assisted Intervention, 2011) the disclosure of which is incorporated herein by reference in its entirety). In another example, the automated image analysis system may annotate the location of the aortic valve point (e.g., using (Zheng, Barbu, Georgescu, Scheuering, & Comaniciu, "Four-Chamber Heart Modeling and Automatic Segmentation for 3D Cardiac CT Volumes Using Marginal Space Learning and Steerable Features," IEEE Transactions on Medical Imaging, Vol. 27, No. 11, pp. 1668-1681, 2008), the disclosure of which is incorporated herein by reference in its entirety). In another example, the automated image analysis system may annotate coronary vessel centerlines (e.g., using (Kitamura, Li, & Ito, "Automatic coronary extraction by supervised detection and shape matching" Biomedical Imaging (ISBI), 2012 9th IEEE International Symposium on May 2-5, 2012), the disclosure of which is incorporated herein by reference in its entirety). In another example, the automated image analysis system may include labeling of the vessel centerlines by vessel name (i.e., RCA, LAD, and LCX). This labeling may be performed by using a set of training labels to determine the statistics of the geometric positioning of each labeled vessel centerline and assigning the vessel centerline the labels having the maximum likelihood based on its geometric position (see e.g., (Lorenz & Berg, "A Comprehensive Shape Model of the Heart" Medical Image Analysis 10 (2006) 657-670, 18 May 2006), the disclosure of which is incorporated herein by reference in its entirety). In another example, the automated image analysis system may annotate 3-D segmentation of the coronary vessel lumen (e.g., using (Schaap, et al. "Robust Shape Regression for Supervised Vessel Segmentation and its Application to Coronary Segmentation in CTA" IEEE Transactions on Medical Imaging, Vol. 30, No. 11, November 2011), the disclosure of which is incorporated herein by reference in its entirety). In another example, the automated image analysis system may annotate a 3-D segmentation of the left ventricle myocardium (e.g., using (Kirisli, et al., 2010)). Any of the above examples may be used individually or in combination.

The image annotation may be presented to the user in any suitable manner, for example the image annotation may be sent via a network to the user's computational device for presentation on an output, such as a monitor, tablet, etc. The image annotation may have any suitable form. For example, the image annotation may be an interactive digital image presented via a graphical user interface (GUI) with various selectable portions for the user to select or deselect in any suitable manner, either by actively selecting or deselecting various portions or doing so passively (e.g. rapidly scrolling over a portion that is acceptable or unacceptable according to any pre-selected user preferences or settings).

The user may review the automated image annotation and provide input/feedback on the image annotation at step 205, such as validation of the image annotation and/or possible correction. The user may provide feedback in any suitable manner, such as by using a GUI. For example, the user may select or deselect various portions of the image annotation to indicate validation and/or correction.

In some embodiments, the image annotation presented to the user may include one or more selectable boxes or icons representing various image annotations. The annotations may be presented to the user in any suitable manner. Some of the annotations may change or be dependent on other annotations. As such, if one of the annotations with a dependency is modified by the user upon review, the automated algorithms for consequent annotations may be re-run with the modified annotation as input. For example, the annotations may be presented to the user in the order:
 a. Aorta segmentation
 b. Ostia points
 c. Aortic valve point
 d. Left ventricle myocardium segmentation
 e. Coronary vessel centerlines
 f. Vessel labeling
 g. Vessel lumen segmentation Based on the input/feedback received from the user on the automated image annotation at step 205 presented to the user at 204, a set of alternative image annotations may be generated at step 206. The feedback may be processed and stored for later use. In some aspects, the user feedback data may be added or aggregated with other user feedback for processing and improving the accuracy of the automated image annotation, using various algorithms, such as machine language algorithms.

The alternative image annotations may be generated in any suitable manner. Examples of alternative image annotations 300 are shown in FIG. 3, and may include using one or more automated image analysis algorithm(s)/systems 302. Examples of automated image analysis algorithm(s)/systems include: face detection in a digital camera, image or video labeling (tagging) in a collection of images/videos (e.g., internet videos), 3-D organ segmentation in CT medical images for radiation therapy planning, 2-D left ventricle segmentation in ultrasound medical images for computing an ejection fraction, 2-D cell detection in a microscopy image for image-based cytometry, 2-D cell tracking through video in an optical microscopy image for determination of mitosis events, 3-D tumor segmentation and feeder vessel centerline annotation in CT medical images for chemoembolization planning, 3-D bone fracture segmentation in CT medical images for bone reconstruction planning, and/or tumor detection and segmentation in a digital mammography application. Another alternative image annotation, as shown in FIG. 3, may include perturbing the image 304 (e.g. via noise, image enhancement, resampling, rotation, scaling, filtering, etc.). Automated image analysis algorithm(s)/systems with a variation of internal parameters 306 may also be used.

In some examples in which an automated image annotation is presented to the user (step 204) prior to generating a set of image annotations for the digital representation of the image data (step 206), the image annotations generated in step 206 maybe alternative image annotations based on input received from the user at step 205. The set of image annotations (which may be alternative image annotations based on input received from the user at step 205) generated at 206 may be processed and an association between members of the set of image annotations (or alternative image annotations based on input received from the user) may be determined at step 208 by using any suitable methods. An example of such a method 400 is shown in FIG. 4, and may include assigning a similarity score between members of a group or cluster of alternative image annotations and/or using a clustering method to determine clusters or groups at step 402. Any suitable algorithm or multiple algorithms may be used to cluster the alternative image annotations, such as by, for example, using hierarchical clustering, and centroid models (e.g. k-means algorithm), etc. In addition or alternatively, an association between the members of the set of alternative image annotations may be determined by assigning alternative image annotations to a group if the alternatives are similar at step 404 and/or members of some other equivalence class.

A representative annotation from one or more groups may be determined at step 210. One or more of the representative annotations for selection may be presented at 212. The annotations may be presented to the user via a GUI or using any other suitable method. The user selection from 212 may be recorded and the image saved at 214 in digital memory. In some aspects, the user selection recorded at step 214 may be processed using various algorithms (e.g. machine learning algorithms) to improve the accuracy of subsequent automated annotations and may be digitally identified, (e.g. using a tag) for use in analyzing user selection behavior. For example, the user selections may be identified by user demographic (e.g. level of experience, attendance of training courses, geographic location), patient information (e.g. chronic disease patient, patient age, gender, etc.), and various other information.

According to one example, fifty different centerlines may be generated at step 206, and each of the centerlines may be processed and assigned a similarity score at step 208, the basis of which may be used to group similar center lines (e.g. centerlines 1-7 and 15-25 may be similar and assigned group A, centerlines 8-14 and 26-35 may be similar and assigned group B, and centerlines 36-50 may be similar and assigned group C). A representative centerline from each group A, B and C, (e.g. centerline 1, 8, and 26) may be determined at 210 and presented to the user at step 212.

In some aspects, the user selection recorded at step 214 may be added to a database of other user selections and processed to determine any associations between the user, patients, and/or any other similarities to improve the accuracy of the automated annotation method, e.g. using any identifying information. For example, it may be determined that users who were trained during a certain time period all make similar selections compared to other users trained at different times, and the method may further include steps to make recommendations to users to improve user accuracy and uniformity in selecting the annotations.

Figure 5:
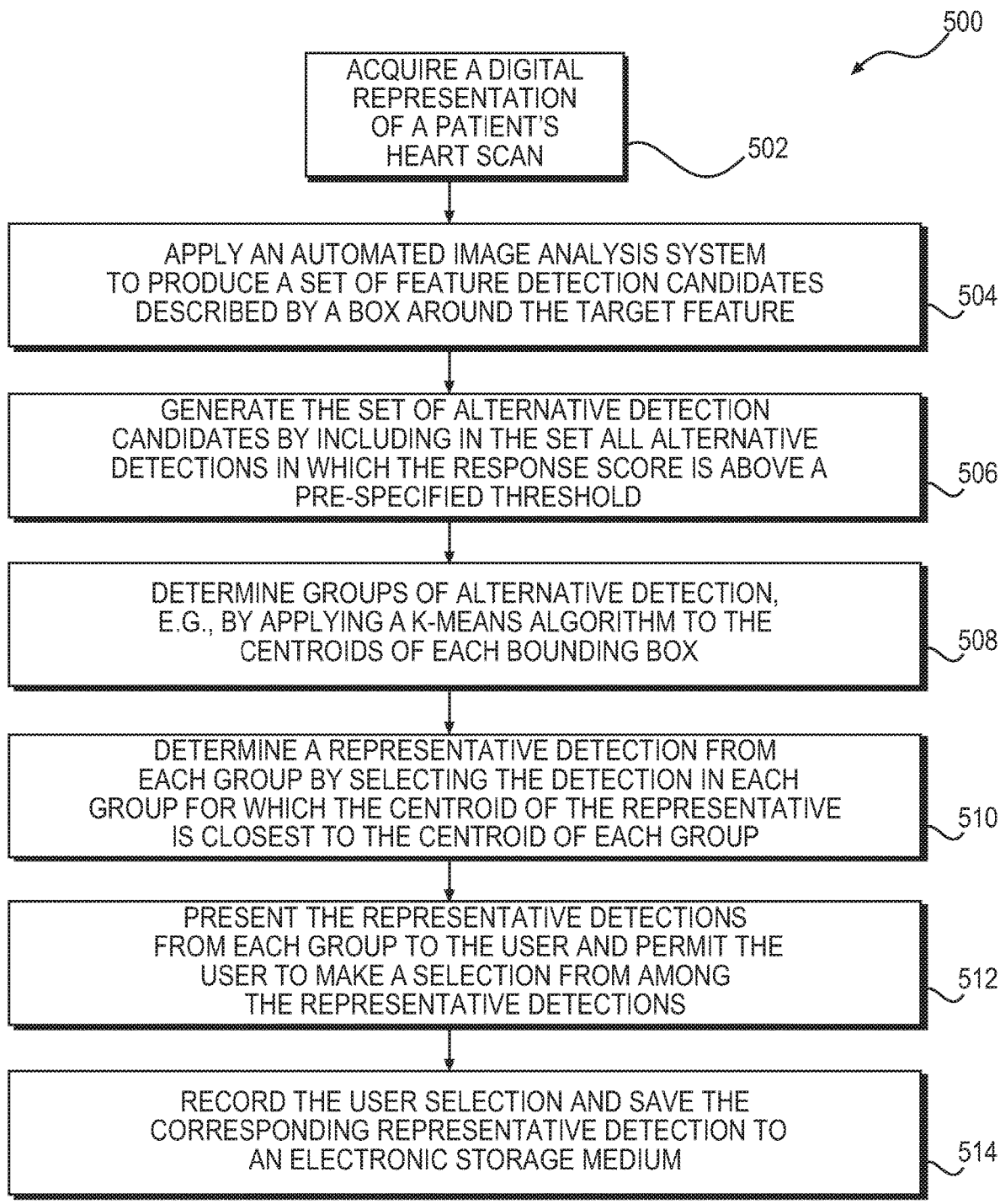
FIG. 5 is a block diagram of an exemplary method for presenting alternative feature detection candidates to a user, according to an exemplary embodiment of the present disclosure.

In another embodiment a similar method as described above and shown in FIG. 2 is shown in FIG. 5. FIG. 5 shows an example of a method 500, which includes applying an automated image analysis system to produce a set of feature detection candidates. The method 500 may include acquiring a digital representation of image data, such as a digital representation of a patient's heart scans in step 502, in a similar manner as described in step 202 above. For example, a digital representation of a patient's heart scan, such as a 3-D cardiac computed tomography (CT) image, may be acquired from the memory or digital storage of a computational device, such as a computer.

The digital representation acquired at step 502 may be analyzed and processed by an automated image analysis system to produce a set of feature detection candidates at step 504. The feature detection candidates may be any suitable target location(s) on the image, such as, for example a certain point or portion of the image, an object (e.g. an anatomical landmark, organ, etc.). Each feature detection candidate may be described on the GUI in any suitable manner. For example, a box, circle, or any other shape may surround the target feature. The target feature may be detected in any suitable manner, such as, for example, by using a Viola-Jones detection system and/or any other suitable feature detection system. The automated image analysis system may include an algorithm, which includes assigning each feature detection box a response score indicating the certainty of the algorithm to the position and size of the box bounding the detected object.

At step 506, a set of alternative detection candidates may be generated in any suitable manner. In one embodiment, the assigned response score for each feature detection calculated in step 504 may be compared to a pre-determined threshold score. The pre-determined threshold score may be adjusted based one or more suitable factors. The set of alternative detections may be generated based on feature detections having an assigned response score equal to or above the pre-determined threshold.

The alternative detection candidates generated in step 506 may be further processed into groups in any suitable manner in step 508. For example, a k-means algorithm or other suitable algorithm may be applied to the centroids of each bounding box of each of the alternative detection candidates.

A representative detection from each group may be determined at step 510. For example, a detection from each group may be selected for which the centroid of the representative is closest (e.g. by Euclidean distance) to the centroid of each group. The representative detections from each group determined at step 510 may be presented to the user at step 512. The user may be permitted to make one or more selections from the representative detection in any suitable manner. The user selection(s) may be saved at step 514 to an electronic storage medium (e.g. hard drive, computer RAM, network communication channel, etc.)

Figure 6:
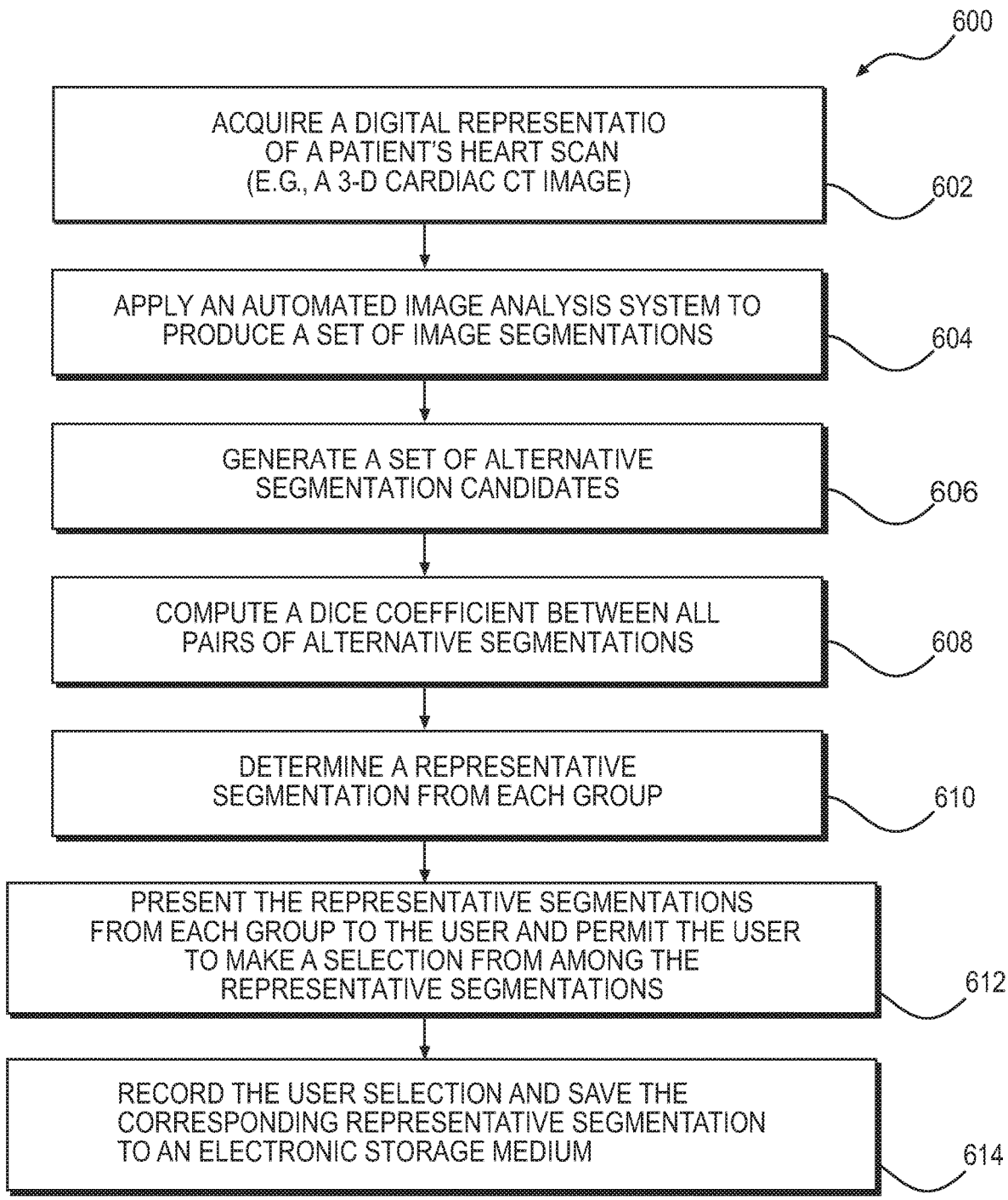
FIG. 6 is a block diagram of an exemplary method for presenting alternative image segmentation candidates to a user, according to an exemplary embodiment of the present disclosure.

In another embodiment, another similar method as described above and shown in FIGS. 2 and 5 is shown in FIG. 6, which shows a method 600 in which image segmentation may be used to automatically correct image annotations. A digital representation of a target object, such as a patient's heart may be acquired at step 602 in any suitable manner, as described above with reference to FIGS. 2 and 5. An automated image analysis system may be applied to produce a set of image segmentation candidates at step 604, for example, by using level set, graph based methods (e.g., graph cuts, random walker), active shape models, and/or active appearance models.

A set of alternative segmentation candidates may be generated at step 606 using any suitable method. Each method may include several parameters. A set of alternative segmentations may therefore be generated by randomly selecting several parameter sets, applying several image segmentation techniques, and perturbing the input image by rigid transformation and the addition of Gaussian noise to the voxels.

A Dice coefficient may be computed at step 608 between all or a portion of pairs of alternative segmentations. Groups of alternative segmentations may be determined by applying a clustering algorithm on the set of alternative segmentations in which the reciprocal of the Dice coefficient may be interpreted as a distance between segmentations. Examples of clustering algorithms include spectral partitioning and isoperimetric portioning.

A representative segmentation from each group determined in step 608 may be determined at step 610. The representative segmentation may be determined by randomly selecting a segmentation from each group, by creating an average segmentation from the segmentations in the group, and/or by selecting the segmentation from the group that is closest (e.g. has the highest Dice overlap) to the average segmentation.

The representative segmentations determined at step 610 may be presented to the user in any suitable manner, for example, via the GUI. The user may then make a selection from among the representative segmentations at step 612.

The user selection at 612 may be recorded and the corresponding representative segmentation may be saved to an electronic storage medium.

Figure 7:
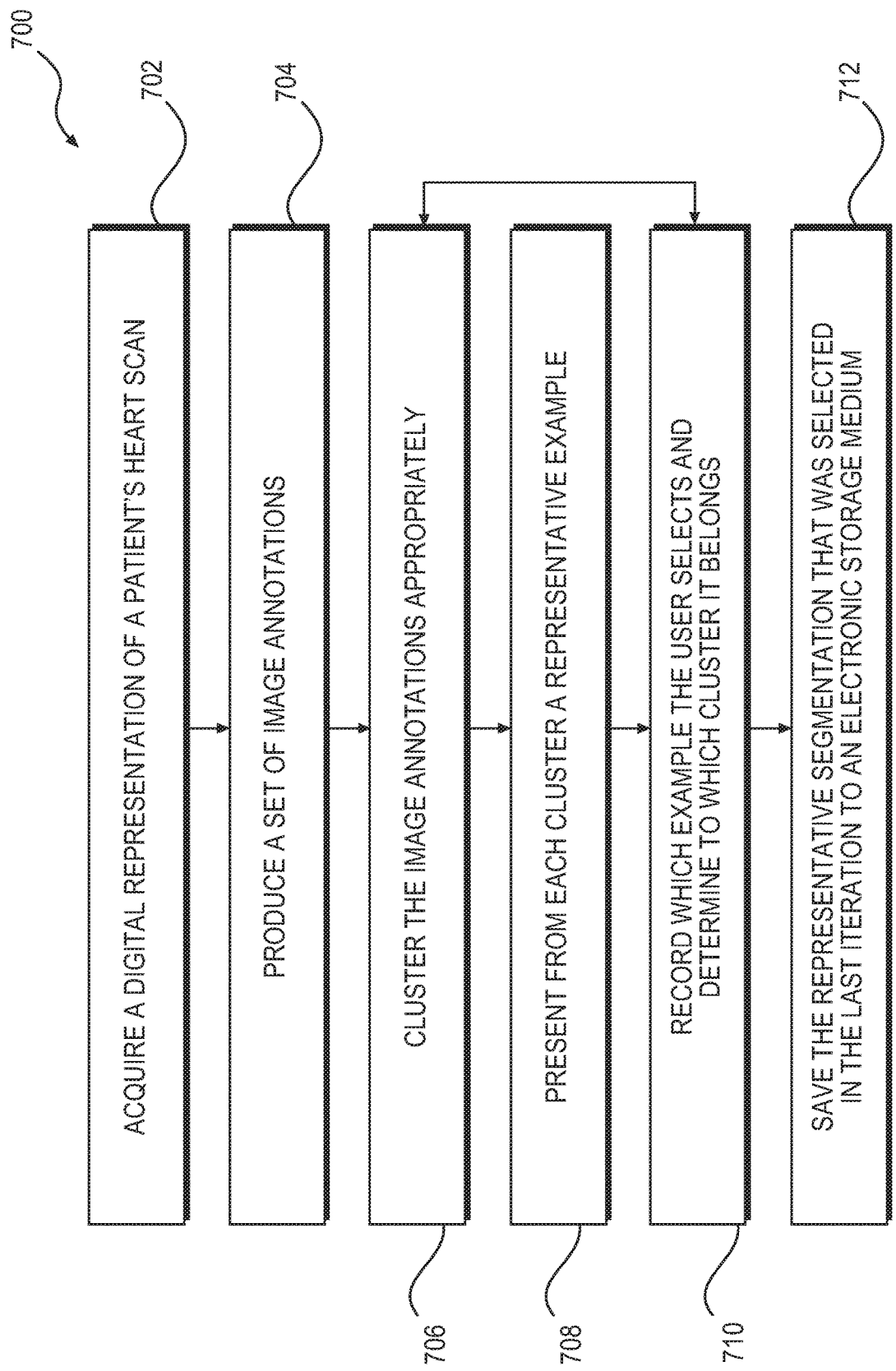
FIG. 7 is a block diagram of an exemplary method for hierarchal image annotation selection, according to an exemplary embodiment of the present disclosure.

In another embodiment, as shown in FIG. 7, a hierarchal selection method 700 may be used to more precisely specify which automatically generated annotation is selected, instead of selecting the automatically determined representative example from one of the groups. The method 700 may be used in conjunction with other methods, such as the feature detection method 500 and image segmentation method 600, as described above. Similar to the method 200 described above, the hierarchal method 700 may include acquiring a digital representation of a target object, such as a patient's heart scan at step 702, and producing a set of image annotations at step 704.

The image annotations may be clustered at step 706 in any suitable manner, such as using by applying a k-means algorithm and/or determining a representative detection as described above in FIG. 5 steps 508-510. A representative example from each cluster may be presented at step 708 in any suitable manner as described in FIG. 5 step 512. The example selected by the user from step 708 may be recorded on a digital storage medium in step 710. Steps 706-710 may be repeated one or more times. Each time the steps 706-710 are repeated, the step may only start with the image annotations that belong to the cluster that was selected. In addition, the image annotations that fall in the same cluster may be generated, and the representative segmentations that were selected in the last iteration may be stored in an electronic storage medium in step 712.

It should be appreciated that any type of computing system, such as a computer having a digital memory storage device, a processor, and any desired user interfaces may be configured to perform the presently disclosed methods. Moreover, any type of servers, clustered computers, and/or cloud computers may be configured to perform the presently disclosed methods. Any of the above referenced devices may be connected to a network, such as the Internet, to receive and transmit data used in performing the presently disclosed methods.

Figure 8:
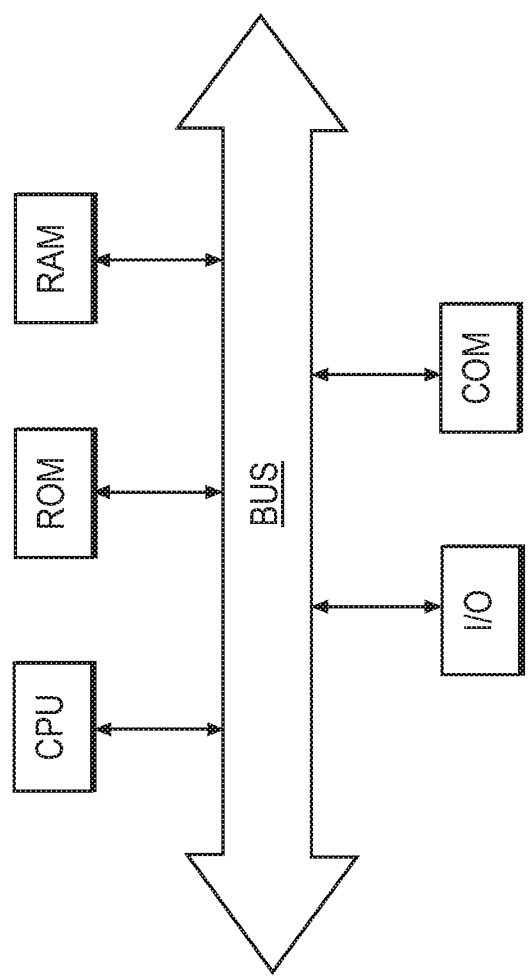
FIG. 8 is a simplified block diagram of an exemplary computer system in which embodiments of the present disclosure may be implemented.

FIG. 8 is a simplified block diagram of an exemplary computer system 800 in which embodiments of the present disclosure may be implemented, for example as any of the physician devices or servers 102, third party devices or servers 104, and server systems 106. A platform for a server 800, for example, may include a data communication interface for packet data communication 860. The platform may also include a central processing unit (CPU) 820, in the form of one or more processors, for executing program instructions. The platform typically includes an internal communication bus 810, program storage, and data storage for various data files to be processed and/or communicated by the platform such as ROM 830 and RAM 840, although the server 800 often receives programming and data via a communications network (not shown). The hardware elements, operating systems, and programming languages of such equipment are conventional in nature, and it is presumed that those skilled in the art are adequately familiar therewith. The server 800 also may include input and output ports 850 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

As described above, the computer system 800 may include any type or combination of computing systems, such as handheld devices, personal computers, servers, clustered computing machines, and/or cloud computing systems. In one embodiment, the computer system 800 may be an assembly of hardware, including a memory, a central processing unit ("CPU"), and/or optionally a user interface. The memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. The CPU may include one or more processors for processing data according to instructions stored in the memory. The functions of the processor may be provided by a single dedicated processor or by a plurality of processors. Moreover, the processor may include, without limitation, digital signal processor (DSP) hardware, or any other hardware capable of executing software. The user interface may include any type or combination of input/output devices, such as a display monitor, touchpad, touchscreen, microphone, camera, keyboard, and/or mouse.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms, such as computer or machine "readable medium" refer to any medium that participates in providing instructions to a processor for execution.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of controlling image annotation, using at least one computer system, the method comprising using a processor for:

receiving a digital representation of image data corresponding to anatomic features of a patient;

segmenting the digital representation to determine a first candidate coronary vessel tree by a method controlled by one or more parameters;

segmenting the digital representation to generate a plurality of alternative candidate coronary vessel trees corresponding to the first candidate coronary vessel tree;

generating a plurality of groups of alternative candidate coronary vessel trees, each group of the plurality of groups comprising a subset of the plurality of alternative candidate coronary vessel trees;

determining, by the at least one computer system, a representative alternative candidate coronary vessel tree for each of the groups of alternative candidate coronary vessel trees, the representative alternative candidate coronary vessel tree for each group being determined as either:
    an alternative candidate coronary vessel tree of the group closest to an average alternative candidate coronary vessel tree of the group, or
    a generated average coronary vessel tree of the group; and
presenting, by the at least one computer system, the first candidate coronary vessel tree and each representative alternative candidate coronary vessel tree for selection and/or correction by a user.

2. The computer-implemented method of claim 1, wherein the plurality of alternative candidate coronary vessel trees are generated by one or more of randomly selecting settings of the one or more parameters, applying a plurality of image segmentation techniques, perturbing the digital representation by rigid transformation, or perturbing the digital representation by an addition of Gaussian noise to the digital representation.

3. The computer-implemented method of claim 1, further comprising:
    determining, by the at least one computer system, one or more associations between alternative candidate coronary vessel trees of the plurality of alternative candidate coronary vessel trees,
    wherein the plurality of groups of alternative candidate coronary vessel trees are generated based on the determined one or more associations.

4. The computer-implemented method of claim 1, wherein the digital representation of image data is acquired electronically via a network.

5. The computer-implemented method of claim 1, wherein each representative coronary vessel tree identifies anatomic features identified within the digital representation of image data.

6. The computer-implemented method of claim 1, wherein the generated first candidate coronary vessel tree is generated using one or more of a level set, a graph based method, an active shape model, an active appearance model.

7. The computer-implemented method of claim 3, wherein each of the one or more associations between alternative candidate coronary vessel trees of the plurality of alternative candidate coronary vessel trees is determined by computing a dice coefficient.

8. The computer-implemented method of claim 1, wherein generating the plurality of groups of alternative candidate coronary vessel trees includes generating the plurality of groups of alternative candidate coronary vessel trees via a cluster algorithm.

9. The computer-implemented method of claim 8, wherein the cluster algorithm includes spectral partitioning and isoperimetric portioning.

10. The computer-implemented method of claim 1, wherein the image data is a portion of a body organ.

11. A system of controlling image annotation, the system comprising:
    a data storage device storing instructions for controlling image segmentation; and
    a processor configured to execute the instruction to perform a method including:
    receiving a digital representation of image data corresponding to anatomic features of a patient;
    segmenting the digital representation to determine a first candidate coronary vessel tree by a method controlled by one or more parameters;
    segmenting the digital representation to generate a plurality of alternative candidate coronary vessel trees corresponding to the first candidate coronary vessel tree;
    generating a plurality of groups of alternative candidate coronary vessel trees, each group of the plurality of groups comprising a subset of the plurality of alternative candidate coronary vessel trees;
    determining a representative alternative candidate coronary vessel tree for each of the groups of alternative candidate coronary vessel trees, the representative alternative candidate coronary vessel tree for each group being determined as either:
        an alternative candidate coronary vessel tree of the group closest to an average alternative candidate coronary vessel tree of the group, or
        a generated average coronary vessel tree of the group; and
    presenting the first candidate coronary vessel tree and each representative alternative candidate coronary vessel tree for selection or correction by a user.

12. The system of claim 11, wherein the plurality of alternative candidate coronary vessel trees are generated by one or more of randomly selecting settings of the one or more parameters, applying a plurality of image segmentation techniques, perturbing the digital representation by rigid transformation, or perturbing the digital representation by an addition of Gaussian noise to the digital representation.

13. The system of claim 11, wherein the processor is further configured to electronically acquire the digital representation of image data via a network.

14. The system of claim 11, wherein the processor is further configured to determine one or more associations between alternative candidate coronary vessel trees of the plurality of alternative candidate coronary vessel trees,
    wherein the plurality of groups of alternative candidate coronary vessel trees are generated based on the determined one or more associations.

15. The system of claim 11, wherein the processor is further configured to automatically generate the first candidate coronary vessel tree using one or more of a level set, a graph based method, an active shape model, an active appearance model.

16. The system of claim 14, wherein the processor is configured to determine each of the one or more associations between alternative candidate coronary vessel trees of the plurality of alternative candidate of coronary vessel trees by computing a dice coefficient.

17. The system of claim 14, wherein processor is configured to generate the plurality of groups of alternative candidate coronary vessels trees via a cluster algorithm.

18. The system of claim 17, wherein the cluster algorithm includes spectral partitioning and isoperimetric portioning.

19. A non-transitory computer-readable medium for use on a computer system containing computer-executable programming instructions for controlling image annotation, the instructions being executable by the computer system for:
    receiving a digital representation of image data corresponding to anatomic features of a patient;
    segmenting the digital representation to determine a first candidate coronary vessel tree by a method controlled by one or more parameters;
    segmenting the digital representation to generate a plurality of alternative candidate coronary vessel trees corresponding to the first candidate coronary vessel tree;

generating a plurality of groups of alternative candidate coronary vessel trees, each group of the plurality of groups comprising a subset of the plurality of alternative candidate coronary vessel trees;

determining, by the computer system, a representative alternative candidate coronary vessel tree for each of the groups of alternative candidate coronary vessel trees, the representative alternative candidate coronary vessel tree for each group being determined as either:

an alternative candidate coronary vessel tree of the group closest to an average alternative candidate coronary vessel tree of the group, or a generated average coronary vessel tree of the group; and presenting, by the computer system, the first candidate coronary vessel tree and each representative alternative candidate coronary vessel tree for selection or correction by a user.

20. The non-transitory computer readable medium of claim 19, the instructions being executable by the computer system further comprising determining one or more associations between alternative candidate coronary vessel trees of the plurality of alternative candidate coronary vessel trees, wherein the plurality of groups of alternative candidate coronary vessel trees are generated based on the determined one or more associations.

* * * * *

UNITED STATES PATENT AND TRADEMARK OFFICE
CERTIFICATE OF CORRECTION

| | | |
|---|---|---|
| PATENT NO. | : 11,742,070 B2 | Page 1 of 1 |
| APPLICATION NO. | : 16/725649 | |
| DATED | : August 29, 2023 | |
| INVENTOR(S) | : Leo Grady and Michiel Schaap | |

It is certified that error appears in the above-identified patent and that said Letters Patent is hereby corrected as shown below:

In the Claims

In Column 12, Line 60, In Claim 1, delete "tree:" and insert --tree;--.

In Column 14, Line 4, In Claim 11, delete "tree:" and insert --tree;--.

In Column 14, Line 67, In Claim 19, delete "tree:" and insert --tree;--.

Signed and Sealed this
First Day of October, 2024

Katherine Kelly Vidal
*Director of the United States Patent and Trademark Office*